US007745411B2

(12) United States Patent
Rodgers et al.

(10) Patent No.: US 7,745,411 B2
(45) Date of Patent: *Jun. 29, 2010

(54) METHODS FOR PROMOTING ERYTHROPOIESIS

(75) Inventors: Kathleen Rodgers, Long Beach, CA (US); Gere diZerega, San Luis Obispo, CA (US)

(73) Assignee: University of Southern California, Los Angeles, CA (US)

( * ) Notice: Subject to any disclaimer, the term of this patent is extended or adjusted under 35 U.S.C. 154(b) by 416 days.

This patent is subject to a terminal disclaimer.

(21) Appl. No.: 11/810,560

(22) Filed: Jun. 6, 2007

(65) Prior Publication Data

US 2009/0062210 A1    Mar. 5, 2009

Related U.S. Application Data

(63) Continuation of application No. 09/658,315, filed on Sep. 8, 2000, now Pat. No. 7,288,522, which is a continuation of application No. 09/245,680, filed on Feb. 8, 1999, now Pat. No. 6,239,109.

(60) Provisional application No. 60/074,106, filed on Feb. 8, 1998, provisional application No. 60/111,535, filed on Dec. 9, 1998.

(51) Int. Cl.
    *A61K 38/08*      (2006.01)
(52) U.S. Cl. .......................................... 514/16; 530/329
(58) Field of Classification Search ........................ None
See application file for complete search history.

(56) References Cited

U.S. PATENT DOCUMENTS

| | | | |
|---|---|---|---|
| 4,987,121 A | 1/1991 | Baertschi et al. | |
| 5,015,629 A | 5/1991 | diZerega et al. | |
| 5,032,507 A | 7/1991 | Yu et al. | |
| 5,104,653 A | 4/1992 | Michalevicz et al. | |
| 5,188,828 A | 2/1993 | Goldberg et al. | |
| 5,378,808 A * | 1/1995 | D'Andrea et al. | 530/350 |
| 5,482,924 A | 1/1996 | Royet et al. | |
| 5,541,158 A | 7/1996 | Vance et al. | |
| 5,610,056 A * | 3/1997 | Nakahata | 435/378 |
| 5,629,292 A | 5/1997 | Rodgers et al. | |
| 5,693,616 A | 12/1997 | Krstenansky et al. | |
| 5,716,935 A | 2/1998 | Rodgers et al. | |
| 5,824,297 A * | 10/1998 | Iwata et al. | 424/85.1 |
| 5,834,432 A | 11/1998 | Rodgers et al. | |
| 5,955,430 A | 9/1999 | Rodgers et al. | |
| 6,083,747 A * | 7/2000 | Wong et al. | 435/325 |
| 6,165,978 A * | 12/2000 | Rodgers et al. | 514/16 |
| 6,239,109 B1 * | 5/2001 | Rodgers et al. | 514/16 |
| 6,335,195 B1 * | 1/2002 | Rodgers et al. | 435/377 |
| 6,566,335 B1 * | 5/2003 | Rodgers et al. | 514/15 |
| 6,762,167 B1 * | 7/2004 | Rodgers et al. | 514/16 |
| 7,288,522 B1 * | 10/2007 | Rodgers et al. | 514/16 |

| | | |
|---|---|---|
| 2004/0120959 A1 | 6/2004 | Tryggvason et al. |

FOREIGN PATENT DOCUMENTS

| | | |
|---|---|---|
| WO | WO 95/08337 | 3/1995 |
| WO | WO 95/08565 | 3/1995 |
| WO | WO 96/39164 | 12/1996 |
| WO | WO 98-32457 | 7/1998 |
| WO | WO 99-26644 | 6/1999 |
| WO | WO 99-31125 | 6/1999 |

OTHER PUBLICATIONS

Kurt R. Reissmann, M.D., (1950), *Blood*, "Studies on the Mechanizm of Erythropoietic Stimulation in Parabiotic Rats During Hypoxia", 8: pp. 349-357.
Allan Erslev, M.D., (1953), *Blood*, "Humoral Regulation of Red Cell Production", 8: pp. 349-357.
Jerry L. Spivak, (1986), *Int. J. Cell Cloning*, "The Mechanism of Action of Erythropoietin", 4: pp. 139-166.
K. Sawada, et al., (1987), *The Journal of Clinical Investigtation, Inc.*, "Purification of Human Erythroid Colony-forming Units and Demonstration of Specific Binding of Erythropoietin", 80: pp. 357-366.
T.S. Kickler, et al., (1988), *J. Am. Med. Assoc.*, "Effect of Repeated Whole Blood Donations on Serum Immunoreactive Erythropoietin Levels in Autologous Donors", 260; pp. 65-67.
Jaime Caro, et al., (1979), *J. Lab. Clin. Med.*, "Erythropoietin Levels in Uremic Nephric and Anephric Patients", 93: pp. 449-458.
Heinz W. Radtke, et al., (1979), *Blood*, "Serum Erythropoietin Concentration in Chronic Renal Failure: Relationship to Degree of Anemia and Excretory Renal Function" 54(4): pp. 877-884.
Manju Chandra, M.D., et al., (1988), *J. Pediatr.*, "Relation of Serum Erythropoietin Levels to Renal Excretory Function: Evidence for Lowered Set Point for Erythropoietin Production in Chronic Renal Failure", 113: pp. 1015-1021.
Joseph W. Eschbach, M.D., et al., (1988), *American Journal of Kidney Diseases*, "Recombinant Human Erythropoietin: Implications for Nephrology" 11: pp. 203-209.

(Continued)

*Primary Examiner*—Anish Gupta
(74) *Attorney, Agent, or Firm*—McDonnell Boehnen Hulbert & Berghoff LLP

(57) ABSTRACT

The present invention provides methods, compounds, pharmaceutical compositions, and kits for the augmentation of erythropoiesis by potentiating erythropoietin-induced differentiation with angiotensinogen, angiotensin I (AI), AI analogues, AI fragments and analogues thereof, angiotensin II analogues, AII fragments or analogues thereof or AII $AT_2$ type 2 receptor agonists as a therapeutic adjunct. The method is useful for the treatment of congenital or acquired aplastic or hypoplastic anemia associated with chronic renal failure, end-stage renal disease, renal transplantation, cancer, AIDS, chemotherapy, radiotherapy, bone marrow transplantation and chronic diseases.

12 Claims, 6 Drawing Sheets

OTHER PUBLICATIONS

Satya P. Kunapuli, et al., (1987),*Circulation Research*, "Molecular Cloning of Human Angiotensinogen cDNA and Evidence for the Presence of Its mRNA in Rat Heart" 60: pp. 786-790.

W.M. Clouston, et al., (1988), *Genomics*, "Molecular Cloning of the Mouse Angiotensinogen Gene", 2: pp. 240-248.

Ryoichiro Kageyama, et al., (1984), *Biochemistry*, "Primary Structure of Human Preangiotensinogen Deduced from the Cloned cDNA Sequence", 23: pp. 3603-3609.

Hiroaki Ohkubo, et al., (1983), *Biochemistry*, "Cloning and Sequence Analysis of cDNA for Rat Angiotensinogen", 80: pp. 2196-2200.

Dinna N. Cruz, M.D., et al., (1996), *American Journal of Kidney Diseases*, "Angiotensin-Converting Enzyme Inhibitor Therapy in Chronic Hemodialysis Patients: Any Evidence of Erythropoietin Resistance?", 28(4): pp. 535-540.

Hirikata, et al., (1986), *Clin. Nephrol.*, "Participation of the Renin-Angiotensin System in the Captopril-Induced Worsening of Anemia in Chronic Hemodialysis Patients", 26: pp. 27-32.

Anne B. Gould, et al., (1980), *J. Lab. Clin. Med.*, "Interrelation of the Renin System and Erythropoietin in Rats", 96: pp. 523-534.

Peter J. Conlon, et al., (1993), *Transplantation*, "The Beneficial Effect of Enalapril on Erythrocytosis After Renal Transplantation", 56: pp. 217-219.

E.M. Anderson, et al., (1997), *Biology of the Neonate*, "Does Angiotensin Play a Role in Human Fetal Erythropoiesis?", 71: pp. 194-197.

B.I. Shand, et al., (1995), *Journal of Human Hypertension*, "Effect of Losartan on Haematology and Haemorheology in Elderly Patients with Essential Hypertension: A Pilot Study", 9: pp. 233-235.

Bruce A. Julian, et al., (1994), *Kidney International*, "Erythropoiesis After Withdrawal of Enalapril in Post-Transplant Erythrocytosis", 46: pp. 1397-1403.

R.S. Gaston, et al., (1993), *Transplantation Proceedings*, "Enalapril: Safe and Effective Therapy for Posttransplant Erythrocytosis", 25(1): pp. 1029-1031.

M.S. Islam, et al., (1990), *Transplant Int.*, "Captopril Induces Correction of Postrenal Transplant Erythremia", 3: pp. 222-225.

L. Rostaing, et al., (1994), *Transplantation Proceedings*, "Erythrocytosis After Renal Transplant: Study of Erythroid Progenitors and Response to Enalapril", 26(1): pp. 280-281.

Michal Mrug, et al., (1997), *The American Society for Clinical Investigation, Inc.*, "Angiotensin II Stimulates Proliferation of Normal Early Erythroid Progenitors", 100(9): pp. 2310-2314.

Fisher, et al., (1968), *Annals New York Academy of Sciences*, "Effects of Angiotensin, Norepinephrine and Renal Artery Constriction on Erythropoietin Production", pp. 308-317.

James W. Fisher, et al., (1967), *The Journal of Pharmacology and Experimental Therapeutics*, "Effects of Angiotensin and Renal Artery Constriction on Erythropoietin Production", 157(3): pp. 618-625.

D.L. Mann, et al., (1966), *P.S.E.B.M.*, "Effect of Renin, Angiotensin II and Aldosterone on Erythropoiesis", 121: pp. 1152-1154.

Yilmaz C. Bilsel, et al., (1963), *P.S.E.B.M.* "Angiotensin II and Erythropoiesis", 114: pp. 475-479.

Ferrario, et al., (1998), *J. Am. Soc. Nephrol.*, "Novel Angiotensin Peptides Regulate Blood Pressure, Endothelial Function, and Natriuresis", 9: pp. 1716-1722.

Shridhar N. Iyer, et al., (1998), *Hypertension*, "Vasodepressor Actions of Angiotensin-(1-7) Unmasked During Combined Treatment with Lisinopril and Losartan", 31: pp. 699-705.

Freeman, et al., (1996), *Hypertension*, "Angiotensin-(1-7) Inhibits Vascular Smooth Muscle Cell Growth ",28: p. 104-108.

Philipp Ambühl, et al., (1994), *Brain Research Bulletin*, "[7-D-ALA]-Angiotensin-(1-7): Selective Antagonism of Angiotensin-(1-7) in the Rat Paraventricular Nucleus", 35(4): pp. 289-291.

Speth and Kim, (1990), *BBRC*, "Discrimination of Two Angiotensin II Receptor Subtypes with a Selective Agonist Analogue of Angiotensin II, p-Aminophenylalanine$^6$ Angiotensin II", 169: pp. 997-1006.

Rose-Marie Catalioto, et al., (1994), *European Journal of Pharmacology*, "Angiotensins Induce the Release of Prostacyclin from Rabbit Vas Deferens: Evidence for Receptor Heterogeity", 256: pp. 93-97.

Susan E. Bryson, et al., (1992), *European Journal of Pharmacology*, "Induction of the Angiotensin $AT_2$ Receptor Subtype Expression by Differentiation of the Neuroblastoma X Glioma Hybrid, NG-108-15", 225: pp. 119-127.

Josef Pfeilschifter, et al., (1992), *European Journal of Pharmacology-Molecular Pharmacology Section*, "Angiotensin II Stimulation of Phospholipase D in Rat Renal Mesangial Cells is Mediated by the $AT_1$ Receptor Subtype", 225: pp. 57-62.

Neelam Jaiswal, et al., (1992), *Hypertension*, "Stimulation of Endothelial Cell Prostaglandin Production by Angiotensin Peptides", 19[*suppl II*]: pp. II-49-II-55.

Richard M. Edwards, et al., (1993), *The Journal of Pharmacology and Experimental Therapeutics*, "Angiotensin II Inhibits Glomerular Adenylate Cyclase via the Angiotensin II Receptor Subtype 1 ($AT$)" 266(2): pp. 506-510.

Neelam Jaiswal, et al, (1993), *The Journal of Pharmacology and Experimental Therapeutics*, "Differential Regulation of Prostaglandin Synthesis by Angiotensin Peptides in Porcine Aortic Smooth Muscle Cells: Subtypes of Angiotensin Receptors Involved[1]", 266(2): pp. 664-673.

Neelam Jaiswal, et al., (1991), *Hypertension*, "Subtype 2 Angiotensin Receptors Mediate Prostaglandin Synthesis in Human Astrocytes", 17: pp. 1115-1120.

Ilkka Pörsti, et al., (1994), *Br. J. Pharmacol*, "Release of Nitric Oxide by Angiotensin-(1-7) from Porcine Coronary Endothelium: Implications for a Novel Angiotensin Receptor", 111: pp. 652-654.

Regoli, et al., (1974), *Pharmacological Reviews*, "Pharmacology of Angiotensin[1]", 262(2): pp. 69-123.

Mrug, et al., (1996), "Angiotensin II Facilitates Erythropoietin-mediated proliferation of early erythroid progenitors", vol. 88, p. 646a.

\* cited by examiner

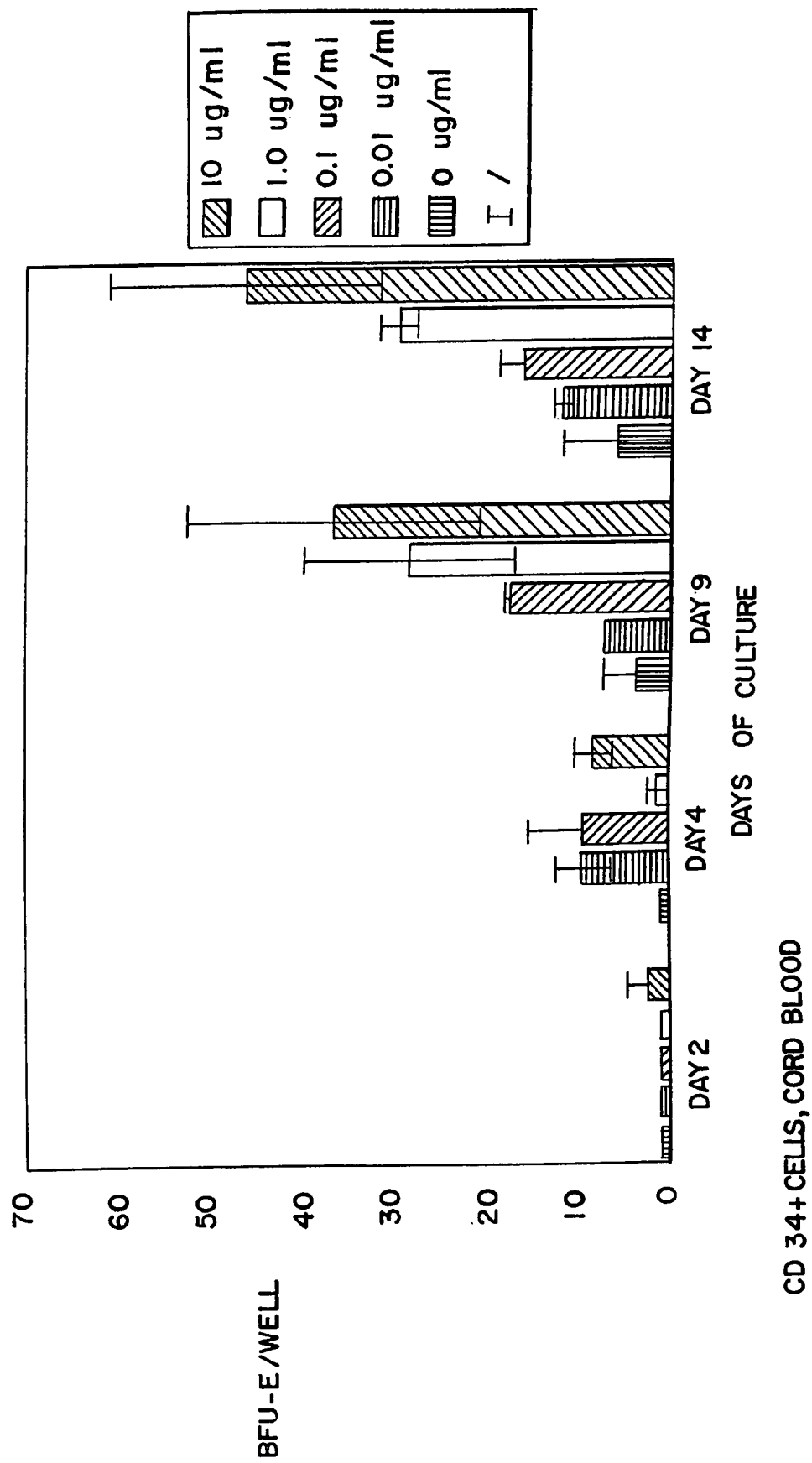

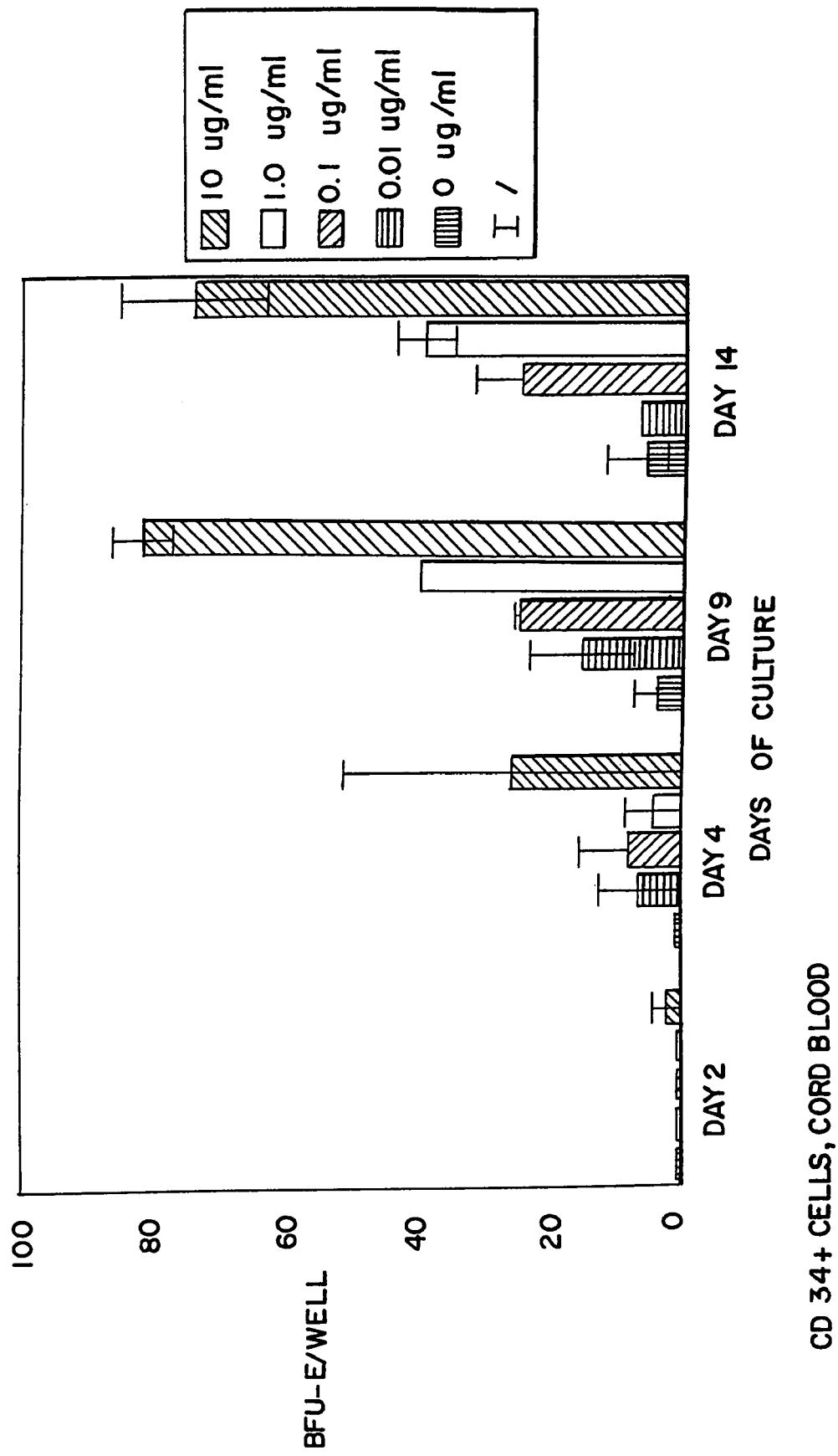

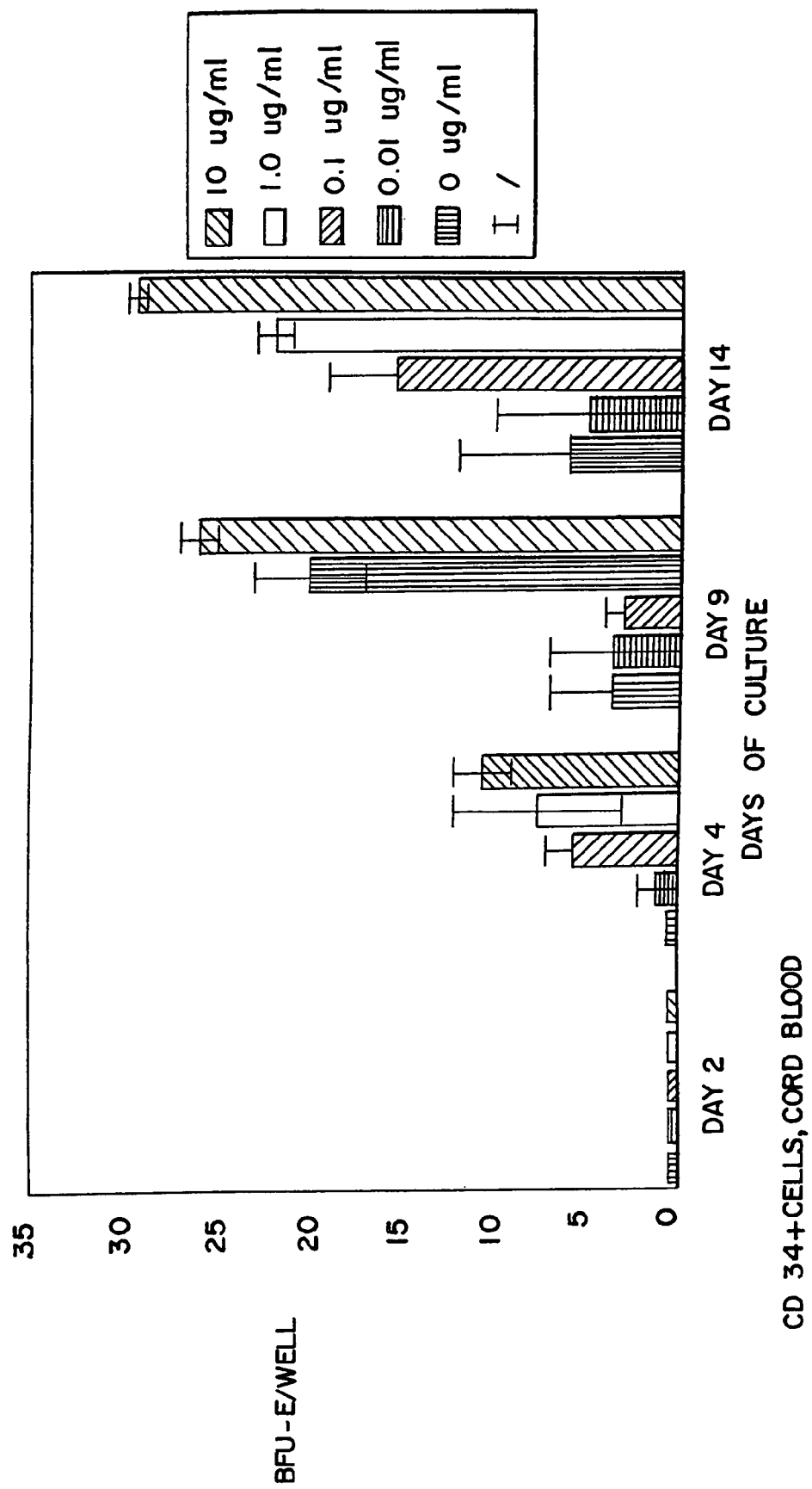

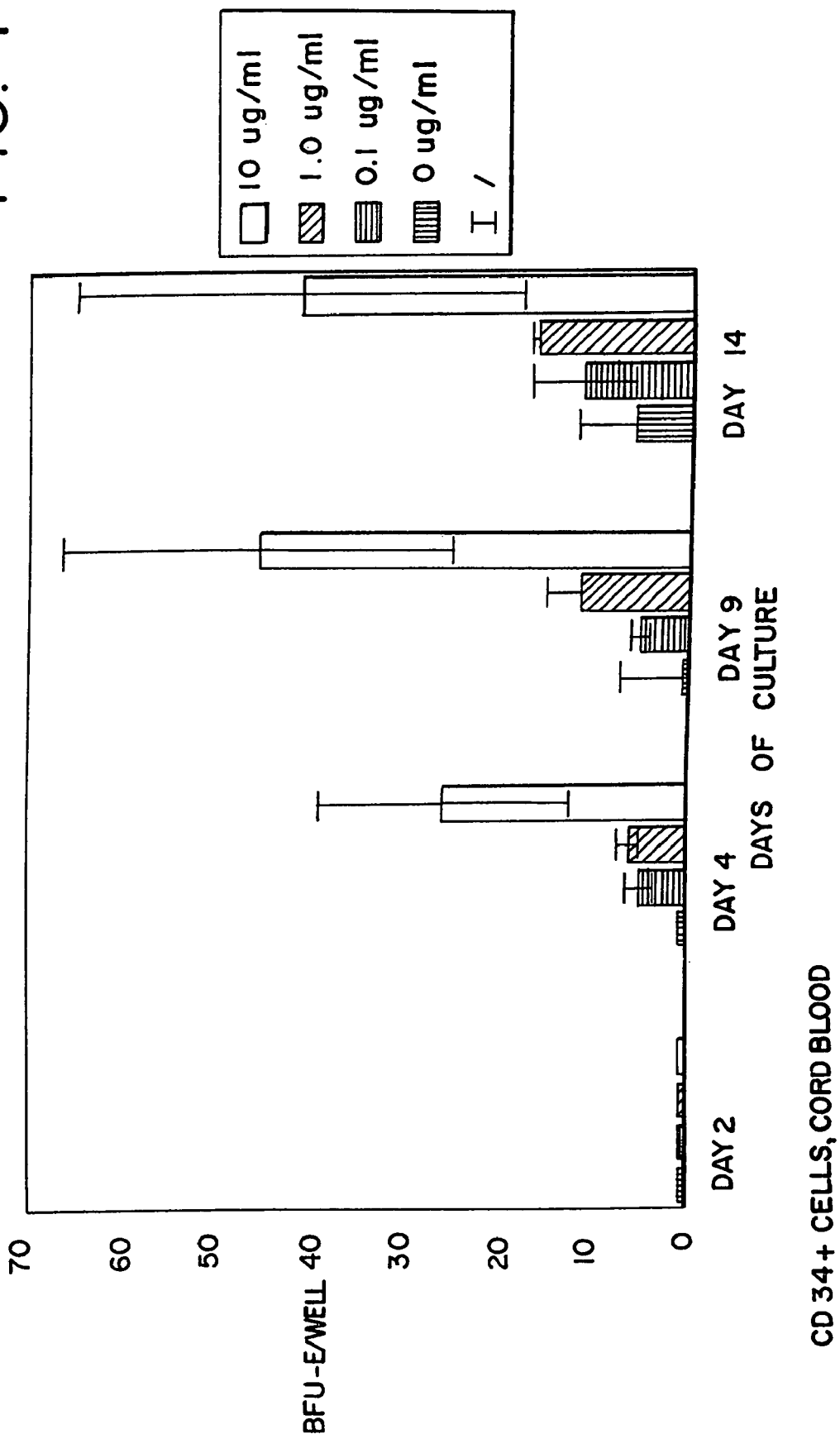

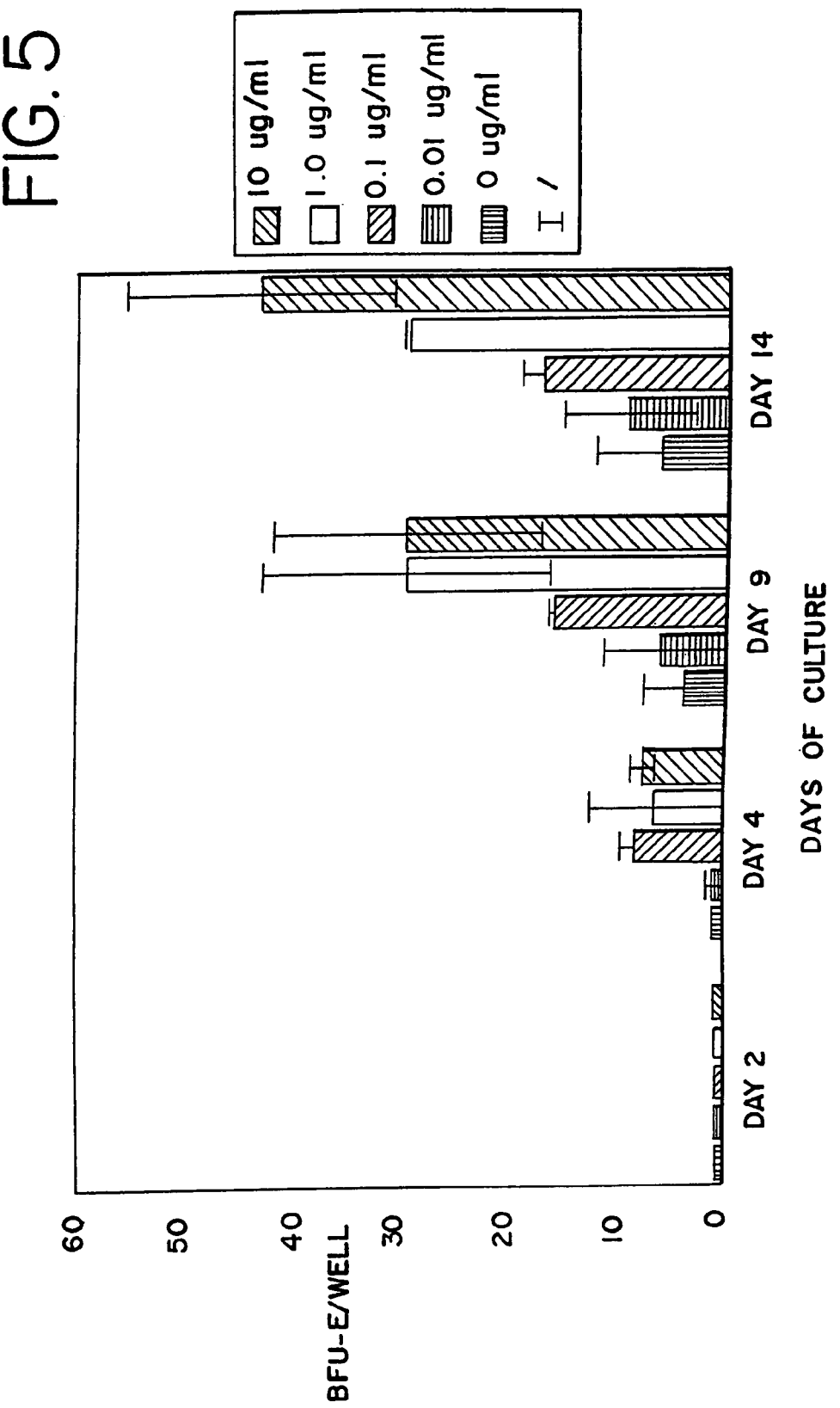

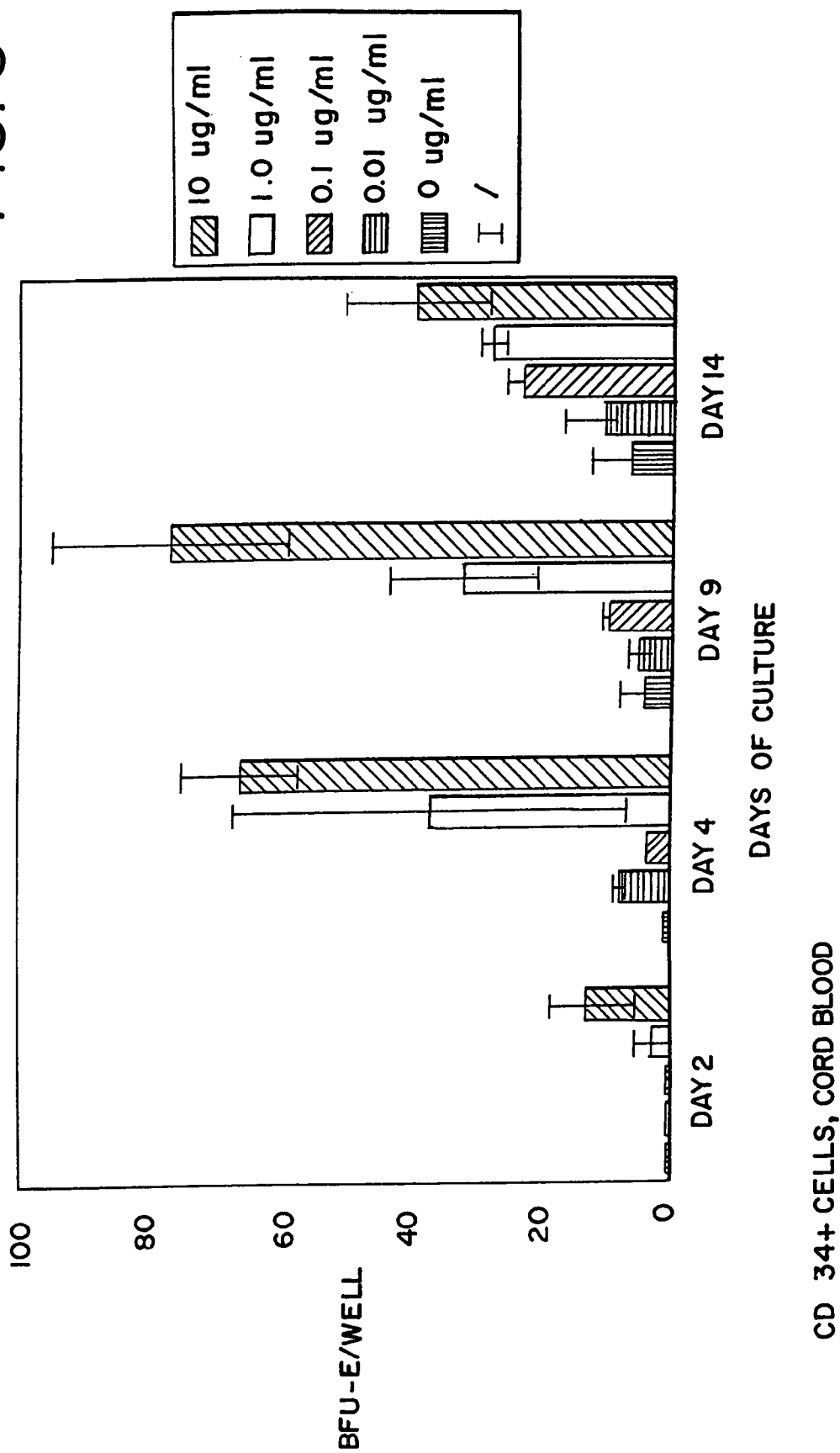

METHODS FOR PROMOTING ERYTHROPOIESIS

CROSS REFERENCE

This application is a continuation-in-part of U.S. Provisional Application Ser. No. 60/074,106 filed Feb. 9, 1998 and a continuation of U.S. Provisional Application Ser. No. 60/111,535 filed Dec. 9, 1998.

FIELD OF THE INVENTION

The present invention relates to compounds, methods, compositions, and kits for the stimulation of erythropoiesis. More specifically, the present invention relates to methods, compositions, and kits that employ effective amounts of angiotensinogen, angiotensin I (AI), AI analogues, AI fragments and analogues thereof, angiotensin II analogues, AII fragments or analogues thereof or AII $AT_2$ type 2 receptor agonists for stimulating erythropoiesis.

BACKGROUND OF THE INVENTION

Maintenance of an adequate supply of oxygen to the body tissues is vital to survival. In the United States alone, several million people suffer from anemia secondary to renal failure, chronic inflammatory disease and malignancies (U.S. Pat. No. 4,987,121, hereby incorporated by reference in its entirety). Since to a large degree the oxygen-carrying capacity of blood is governed by the concentration of erythrocytes in the blood, the appropriate regulation of erythropoiesis is also crucial.

The early studies of Reissmann (Reissmann, K. R., *Blood* 5:372-80 (1950)) and Erslev (Erslev, A., *Blood* 8:349-57 (1953)) clearly demonstrated the hypoxia-induced stimulation of erythropoietin secretion. When erythropoietin is secreted from the erythropoietin-producing cells in response to hypoxia, it travels through the blood to its target organ, the hematopoietic tissues. In humans, the principal hematopoietic tissue is within the liver before birth, and in the bone marrow after birth. (Id.) There, erythropoietin binds specifically to its receptor on the erythroid progenitor cells called burst forming unit-erythroid (BFU-E) and colony-forming unit-erythroid (CFU-E) and stimulates these cells to proliferate and differentiate (Spivak, J. L., *Int. J. Cell Cloning* 4:139-66 (1986)). BFU-E are the earliest erythroid progenitors and constitute 0.01%, approximately, of the nucleated bone marrow cells. CFU-E are derived from BFU-E, account for about 0.1% of marrow cells, and are much more responsive to erythropoietin than are BFU-E (Spivak, J. L., supra); Sawada, K., et al., *J. Clin. Invest.* 80:357-66 (1987)).

The low erythropoietin levels always present appear sufficient for a basal erythropoiesis rate. Relatively small losses of blood do not appear to stimulate increased erythropoietin production (Kickler, T. S., et al., *J. Am. Med. Assoc.* 260:65-7 (1988)). It is only after a major blood loss that there is an increased production of erythropoietin and rate of erythropoiesis.

It has been well-established that the majority of patients with renal insufficiency and anemia have serum erythropoietin levels well below what would be expected for the degree of anemia (Caro, J., et al., *J. Lab. Clin. Med.* 93:449-58 (1979); Radtke, H. W., et al., Blood 54:877-84 (1979); Chandra, M., et al., *J. Pediatr.* 113:1015-21 (1988)), although they can still respond to hypoxia with an increase in serum erythropoietin levels (Radtke, H. W., et al., *Blood* 54:877-84 (1979); Chandra, M., et al., *J Pediatr* 113:1015-21 (1988)). However, this markedly blunted erythropoietin response substantially contributes to the pathogenesis of the anemia (Eschbach, J. W., et al., *Am J Kid Dis* 11:203-9 (1988)). As a result, patients suffering from chronic renal failure and end-stage renal disease, or those undergoing renal transplantation, develop severe anemia and require regular blood transfusions (Royet, U.S. Pat. No. 5,482,924).

The use of recombinant human erythropoietin has facilitated treatment of these patients. However, recombinant erythropoietin treatment is extremely costly, and methods that augment the effect of erythropoiesis will permit the use of smaller doses of erythropoietin, and thus will decrease treatment costs. Additionally, increasing the rate of erythropoiesis would significantly improve clinical benefits for the treatment of congenital or acquired aplastic or hypoplastic anemia associated with chronic renal failure, end-stage renal disease, renal transplantation, cancer, AIDS, chemotherapy, radiotherapy, bone marrow transplantation and chronic diseases.

SUMMARY OF THE INVENTION

In one aspect, the present invention provides compounds and methods for the augmentation of erythropoiesis by potentiating erythropoietin-induced differentiation with angiotensinogen, angiotensin I (AI), AI analogues, AI fragments and analogues thereof, angiotensin II analogues, AII fragments or analogues thereof or AII $AT_2$ type 2 receptor agonists as a therapeutic adjunct.

In another aspect, the present invention provides pharmaceutical compositions comprising angiotensinogen, angiotensin I (AI), AI analogues, AI fragments and analogues thereof, angiotensin II analogues, AII fragments or analogues thereof or AII $AT_2$ type 2 receptor agonists together with erythropoietin and a pharmaceutically acceptable carrier.

In a further aspect, the present invention provides kits for promoting erythropoiesis, wherein the kits comprise an effective amount of angiotensinogen, AI, AI analogues, AI fragments and analogues thereof, AII analogues, AII fragments or analogues thereof or AII $AT_2$ type 2 receptor agonists, and instructions for using the amount effective of active agent as a therapeutic adjunct to erythropoietin treatment.

In another aspect, the invention provides improved cell culture medium for promoting erythropoiesis, comprising adding an effective amount of the active agents of the invention to promote erythropoiesis.

The methods and kits of the present invention are clinically useful as a therapeutic adjunct for increasing red blood cell production in treating congenital or acquired aplastic or hypoplastic anemia.

BRIEF DESCRIPTION OF THE FIGURES

FIG. 1 is a graph showing the effect of 1GD on formation of human burst-forming units-erythroid.

FIG. 2 is a graph showing the effect of 24B on formation of human burst-forming units-erythroid.

FIG. 3 is a graph showing the effect of 2GD on formation of human burst-forming units-erythroid.

FIG. 4 is a graph showing the effect of 5GD on formation of human burst-forming units-erythroid.

FIG. 5 is a graph showing the effect of AII(1-7) on formation of human burst-forming units-erythroid.

FIG. 6 is a graph showing the effect of AII on formation of human burst-forming units-erythroid.

DETAILED DESCRIPTION OF THE PREFERRED EMBODIMENTS

All cited patents, patent applications and references are hereby incorporated by reference in their entirety.

As defined herein, the term "erythropoiesis" refers to red blood cell production.

As defined herein, "augmentation of erythropoiesis" may occur either by direct stimulation of erythroid production, by increasing erythropoietin production, or by any other mechanism.

Unless otherwise indicated, the term "active agents" as used herein refers to the group of compounds comprising angiotensinogen, angiotensin I (AI), AI analogues, AI fragments and analogues thereof, angiotensin II analogues, AII fragments or analogues thereof and AII $AT_2$ type 2 receptor agonists.

The biological formation of angiotensin is initiated by the action of renin on the plasma substrate angiotensinogen (*Circulation Research* 60:786-790 (1987); Clouston et al., *Genomics* 2:240-248 (1988); Kageyama et al., *Biochemistry* 23:3603-3609; Ohkubo et al., *Proc. Natl. Acad. Sci.* 80:2196-2200 (1983); all references hereby incorporated in their entirety). The substance so formed is a decapeptide called angiotensin I (AI) which is converted to AII by the converting enzyme angiotensinase which removes the C-terminal His-Leu residues from AI (Asp-Arg-Val-Tyr-Ile-His-Pro-Phe-His-Leu [SEQ ID NO:37]). AII is a known pressor agent and is commercially available.

Angiotensin-converting enzyme (ACE) inhibitors have been observed to exacerbate anemia in patients with chronic renal failure and end-stage renal disease (ESRD), as well as in renal transplant recipients (Cruz et al., *Am. J. Kidney Diseases* 28:535-540 (1996); herein incorporated by reference in its entirety). ACE inhibitors appear to induce anemia by decreasing red blood cell production (Id.) Some data exist which suggest that ACE inhibitors may reduce red blood cell production by inhibiting angiotensin-mediated erythropoietin synthesis. (Hirikata et al., *Clin. Nephrol.* 26:27-32 (1986); Gould et al., *J. Lab. Clin. Med.* 96:523-534 (1980); Conlon et al., *Transplantation* 56:217-219 (1993)). However, other studies show that ACE inhibitors do not inhibit erythropoietin synthesis, and suggest that angiotensin does not play a role in erythropoiesis. (Cruz et al., 1996; Anderson et al., *Biology of the Neonate* 71:194-197 (1997); Shand et al., *J. Hum. Hypertension* 9:233-235 (1995); Julian et al., *Kidney Int.* 46:1397-1403 (1994); Gaston et al., *Transplant Proc.* 25:1029-1031 (1993); Islam et al., *Transplant Int.* 3:222-225 (1990); Rostaing et al., *Transplant Proc.* 26:280-281 (1994)). Thus, it is unclear whether AII, or any AII analogues and fragments, stimulate production of erythropoietin.

A recent study suggests that activation of the AT1 receptor with angiotensin II enhances erythropoietin-stimulated human erythroid proliferation in vitro. (Mrug et al., *J. Clin. Invest.* 100 (9):2310-2314 (1997). Previous studies have indicated that slow infusion of angiotensin II in dogs (Fisher et al., in Annals New York Academy of Sciences, pp. 308-317: 1968) and mice (Fisher et al., *J. Pharmacol. and Exper. Therapeutics* 157:618-625, 1967) led to increased erythropoietin production, while injections of angiotensin II into mice and rats did not lead to such an increase. (Mann et al., P.S.E.B.M. 121:1152-1154 (1966); Bilsel et al., P.S.E.B.M. 114:475-479 (1963)). Thus, there is some evidence that angiotensin II (AII) stimulates erythropoiesis in vitro, while the in vivo data is unclear. However, there is no data suggesting whether any AII analogues and fragments also stimulate erythropoiesis, whether in vitro or in vivo. For example, data suggests that the AII fragment AII(1-7) acts through a receptor(s) that is distinct from the AT1 and AT2 receptors which modulate AII activity. (Ferrario et al., *J. Am. Soc. Nephrol.* 9:1716-1722 (1998); Iyer et al., *Hypertension* 31:699-705 (1998); Freeman et al., *Hypertension* 28:104 (1996); Ambuhl et al., *Brain Res. Bull.* 35:289 (1994). Thus, the stimulatory effect of AII through activation of the AT1 receptor reported by Mrug et al. (see above) does not shed any light on the potential stimulatory effect of AII(1-7).

U.S. Pat. No. 5,015,629 to DiZerega (the entire disclosure of which is hereby incorporated by reference) describes a method for increasing the rate of healing of wound tissue, comprising the application to such tissue of angiotensin II (AII) in an amount which is sufficient for said increase. The application of AII to wound tissue significantly increases the rate of wound healing, leading to a more rapid re-epithelialization and tissue repair. The term AII refers to an octapeptide present in humans and other species having the sequence Asp-Arg-Val-Tyr-Ile-His-Pro-Phe [SEQ ID NO:1]. The use of AII analogues and fragments, AT2 agonists, as well as AIII and AIII analogues and fragments in wound healing has also been described. (U.S. Pat. No. 5,629,292; U.S. Pat. No. 5,716,935; WO 96/39164; all references herein incorporated by reference in their entirety.)

A peptide agonist selective for the AT2 receptor (AII has 100 times higher affinity for AT2 than AT1) has been identified. This peptide is p-aminophenylalanine-6-AII ["(p-$NH_2$-Phe)-6-AII)"], Asp-Arg-Val-Tyr-Ile-Xaa-Pro-Phe [SEQ ID NO.36] wherein Xaa is p-$NH_2$-Phe (Speth and Kim, BBRC 169:997-1006 (1990)). This peptide gave binding characteristics comparable to AT2 antagonists in the experimental models tested (Catalioto, et al., *Eur. J. Pharmacol.* 256:93-97 (1994); Bryson, et al., *Eur. J. Pharmacol.* 225:119-127 (1992)).

Many studies have focused upon AII (1-7) (AII residues 1-7) or other fragments of AII to evaluate their activity. AII (1-7) elicits some, but not the full range of effects elicited by AII. Pfeilschifter, et al., *Eur. J. Pharmacol.* 225:57-62 (1992); Jaiswal, et al., *Hypertension* 19 (Supp. II):II-49-II-55 (1992); Edwards and Stack, *J. Pharmacol. Exper. Ther.* 266:506-510 (1993); Jaiswal, et al., *J. Pharmacol. Exper. Ther.* 265:664-673 (1991); Jaiswal, et al., *Hypertension* 17:1115-1120 (1991); Portsi, et al., *Br. J. Pharmacol.* 111:652-654 (1994).

The active AII analogues, fragments of AII and analogues thereof of particular interest in accordance with the present invention are characterized as comprising a sequence consisting of at least three contiguous amino acids of groups $R^1$-$R^8$ in the sequence of general formula I

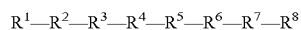

in which $R^1$ and $R^2$ together form a group of formula

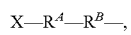

wherein X is H or a one to three peptide group, $R^A$ is suitably selected from Asp, Glu, Asn, Acpc (1-aminocyclopentane carboxylic acid), Ala, $Me^2$Gly, Pro, Bet, Glu($NH_2$), Gly, Asp($NH_2$) and Suc, $R^B$ is suitably selected from Arg, Lys, Ala, Orn, Ser(Ac), Sar, D-Arg and D-Lys;

$R^3$ is selected from the group consisting of Val, Ala, Leu, Lys, norLeu, Ile, Gly, Pro, Aib, Acpc and Tyr;

$R^4$ is selected from the group consisting of Tyr, Tyr($PO_3$)$_2$, Thr, Ser, Ala, homoSer and azaTyr;

R⁵ is selected from the group consisting of Ile, Ala, Leu, norLeu, Val and Gly;

R⁶ is His, Arg or 6-NH₂—Phe;

R⁷ is Pro or Ala; and

R³ is selected from the group consisting of Phe, Phe(Br), Ile and Tyr, excluding sequences including R⁴ as a terminal Tyr group.

Compounds falling within the category of AT2 agonists useful in the practice of the invention include the AII analogues set forth above subject to the restriction that R⁶ is p-NH₂-Phe.

Particularly preferred combinations for $R^A$ and $R^B$ are Asp-Arg, Asp-Lys, Glu-Arg and Glu-Lys. Particularly preferred embodiments of this class include the following: AIII, Arg-Val-Tyr-Ile-His-Pro-Phe [SEQ ID NO:2]; AII(3-8), also known as des1-AIII or AIV, Val-Tyr-Ile-His-Pro-Phe [SEQ ID NO:3]; AII(1-7), Asp-Arg-Val-Tyr-Ile-His-Pro {SEQ ID NO:4]; AII(2-7). Arg-Val-Tyr-Ile-His-Pro [SEQ ID NO:5]; AII(3-7), Val-Tyr-Ile-His-Pro [SEQ ID NO:6]; AII(5-8), Ile-His-Pro-Phe [SEQ ID NO:7]; AII(1-6), Asp-Arg-Val-Tyr-Ile-His [SEQ ID NO:8]; AII(1-5), Asp-Arg-Val-Tyr-Ile [SEQ ID NO:9]; AII(1-4), Asp-Arg-Val-Tyr [SEQ ID NO:10]; and AII (1-3), Asp-Arg-Val [SEQ ID NO:11]. Other preferred embodiments include: Arg-norLeu-Tyr-Ile-His-Pro-Phe [SEQ ID NO:12] and Arg-Val-Tyr-norLeu-His-Pro-Phe [SEQ ID NO:13]. Still another preferred embodiment encompassed within the scope of the invention is a peptide having the sequence Asp-Arg-Pro-Tyr-Ile-His-Pro-Phe [SEQ ID NO:31]. AII(6-8), His-Pro-Phe [SEQ ID NO:14] and AII(4-8), Tyr-Ile-His-Pro-Phe [SEQ ID NO:15] were also tested and found not to be effective.

A further class of particularly preferred compounds in accordance with the present invention consists of those with the following general structure:

ASP-ARG-R1-R2-R3-R4-PRO-R5 wherein R1 is selected from the group consisting of Val, Pro, and Lys;

R2 is selected from the group consisting of Tyr, Tyr (PO₃)₂ and Ala;

R³ is selected from the group consisting of Ile, Val, Leu, norLeu and Ala;

R⁴ is selected from the group consisting of His and Arg; and

R⁵ is either Phe or is absent, and wherein the active agent is not AII.

Preferred embodiments of this class of the invention include SEQ ID NO:4, SEQ ID NO:19, SEQ ID NO:26, SEQ ID NO:27, SEQ ID NO:31, SEQ ID NO: 32, SEQ ID NO: 34; SEQ ID NO:38, SEQ ID NO:39, and SEQ ID NO. 40. Particularly preferred embodiments of this class include SEQ ID NO:4, SEQ ID NO. 31, SEQ ID NO 38, and SEQ ID NO. 39.

Another class of compounds of particular interest in accordance with the present invention are those of the general formula II

R¹—R²—R³—R⁴—R⁵—R⁶—R⁷—R⁸ in which R² is selected from the group consisting of H, Arg, Lys, Ala, Orn, Ser(Ac), Sar, D-Arg and D-Lys;

R³ is selected from the group consisting of Val, Ala, Leu, norLeu, Ile, Gly, Pro, Aib, Acpc and Tyr;

R⁴ is selected from the group consisting of Tyr, Tyr(PO₃)₂, Thr, Ser, homoSer and azaTyr;

R⁵ is selected from the group consisting of Ile, Ala, Leu, norLeu, Val and Gly;

R¹ is His, Arg or 6-NH₂-Phe;

R⁷ is Pro or Ala; and

R⁸ is selected from the group consisting of Phe, Phe(Br), Ile and Tyr.

A particularly preferred subclass of the compounds of general formula II has the formula R²-R³-Tyr-R⁵-His-Pro-Phe   [SEQ ID NO: 16]

wherein R², R³ and R⁵ are as previously defined. Particularly preferred is angiotensin III of the formula Arg-Val-Tyr-Ile-His-Pro-Phe [SEQ ID NO:2]. Other preferred compounds include peptides having the structures Arg-Val-Tyr-Gly-His-Pro-Phe [SEQ ID NO:17] and Arg-Val-Tyr-Ala-His-Pro-Phe [SEQ ID NO:18]. The fragment AII(4-8) was ineffective in repeated tests; this is believed to be due to the exposed tyrosine on the N-terminus.

In the above formulas, the standard three-letter abbreviations for amino acid residues are employed. In the absence of an indication to the contrary, the L-form of the amino acid is intended. Other residues are abbreviated as follows:

TABLE 1

Abbreviation for Amino Acids

| | |
|---|---|
| Me²Gly | N,N-dimethylglycyl |
| Bet | 1-carboxy-N,N,N-trimethylmethanaminium hydroxide inner salt (betaine) |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |

It has been suggested that AII and its analogues adopt either a gamma or a beta turn (Regoli, et al., Pharmacological Reviews 26:69 (1974). In general, it is believed that neutral side chains in position R³, R⁵ and R⁷ may be involved in maintaining the appropriate distance between active groups in positions R⁴, R⁶ and R⁸ primarily responsible for binding to receptors and/or intrinsic activity. Hydrophobic side chains in positions R³, R⁵ and R⁸ may also play an important role in the whole conformation of the peptide and/or contribute to the formation of a hypothetical hydrophobic pocket.

Appropriate side chains on the amino acid in position R² may contribute to affinity of the compounds for target receptors and/or play an important role in the conformation of the peptide. For this reason, Arg and Lys are particularly preferred as R².

For purposes of the present invention, it is believed that R³ may be involved in the formation of linear or nonlinear hydrogen bonds with R⁵ (in the gamma turn model) or R⁶ (in the beta turn model). R³ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, R³ may suitably be selected from Val, Ala, Leu, norLeu, Ile, Gly, Pro, Aib, Acpc and Tyr. Furthermore, Lys has surprisingly been found to be suitable at R³ (see Examples).

With respect to R⁴, conformational analyses have suggested that the side chain in this position (as well as in R³ and R⁵) contribute to a hydrophobic cluster believed to be essential for occupation and stimulation of receptors. Thus, R⁴ is preferably selected from Tyr, Thr, Tyr (PO₃)₂, homoSer, Ser and azaTyr. Furthermore, Ala has surprisingly been found to be suitable at the $R^4$ position (See Examples). In this position, Tyr is particularly preferred as it may form a hydrogen bond with the receptor site capable of accepting a hydrogen from the phenolic hydroxyl (Regoli, et al. (1974), supra).

In position $R^5$, an amino acid with a β aliphatic or alicyclic chain is particularly desirable. Therefore, while Gly is suitable in position $R^5$, it is preferred that the amino acid in this position be selected from Ile, Ala, Leu, norLeu, Gly and Val.

In the AI and AII analogues, fragments and analogues of fragments of particular interest in accordance with the present invention, $R^6$ is His, Arg or 6-$NH_2$—Phe. The unique properties of the imidazole ring of histidine (e.g., ionization at physiological pH, ability to act as proton donor or acceptor, aromatic character) are believed to contribute to its particular utility as $R^6$. For example, conformational models suggest that His may participate in hydrogen bond formation (in the beta model) or in the second turn of the antiparallel structure by influencing the orientation of $R^7$. Similarly, it is presently considered that $R^7$ should be Pro in order to provide the most desirable orientation of $R^8$. In position $R^8$, both a hydrophobic ring and an anionic carboxyl terminal appear to be particularly useful in binding of the analogues of interest to receptors; therefore, Tyr and especially Phe are preferred for purposes of the present invention.

Analogues of particular interest include the following:

demic Press, New York, (1973) for solid phase synthesis and E. Schroder and K. Lubke, The Peptides, Vol. 1, Academic Press, New York, (1965) for solution synthesis. The disclosures of the foregoing treatises are incorporated by reference herein.

In general, these methods involve the sequential addition of protected amino acids to a growing peptide chain (U.S. Pat. No. 5,693,616, herein incorporated by reference in its entirety). Normally, either the amino or carboxyl group of the first amino acid and any reactive side chain group are protected. This protected amino acid is then either attached to an inert solid support, or utilized in solution, and the next amino acid in the sequence, also suitably protected, is added under conditions amenable to formation of the amide linkage. After all the desired amino acids have been linked in the proper sequence, protecting groups and any solid support are removed to afford the crude polypeptide. The polypeptide is desalted and purified, preferably chromatographically, to yield the final product.

In one aspect, the present invention provides methods for the augmentation of erythropoiesis by potentiating erythropoietin-induced differentiation with angiotensinogen, angiotensin I (AI), AII analogues, AI fragments and analogues thereof, angiotensin II analogues, AII fragments or analogues thereof or AII $AT_2$ type 2 receptor agonists (ie: "active

TABLE 2

Angiotensin II Analogues

| AII Analogue Name | Amino Acid Sequence | Sequence Identifier |
|---|---|---|
| Analogue 1 | Asp-Arg-Val-Tyr-Val-His-Pro-Phe | SEQ ID NO: 19 |
| Analogue 2 | Asn-Arg-Val-Tyr-Val-His-Pro-Phe | SEQ ID NO: 20 |
| Analogue 3 | Ala-Pro-Gly-Asp-Arg-Ile-Tyr-Val-His-Pro-Phe | SEQ ID NO: 21 |
| Analogue 4 | Glu-Arg-Val-Tyr-Ile-His-Pro-Phe | SEQ ID NO: 22 |
| Analogue 5 | Asp-Lys-Val-Tyr-Ile-His-Pro-Phe | SEQ ID NO: 23 |
| Analogue 6 | Asp-Arg-Ala-Tyr-Ile-His-Pro-Phe | SEQ ID NO: 24 |
| Analogue 7 | Asp-Arg-Val-Thr-Ile-His-Pro-Phe | SEQ ID NO: 25 |
| Analogue 8 | Asp-Arg-Val-Tyr-Leu-His-Pro-Phe | SEQ ID NO: 26 |
| Analogue 9 | Asp-Arg-Val-Tyr-Ile-Arg-Pro-Phe | SEQ ID NO: 27 |
| Analogue 10 | Asp-Arg-Val-Tyr-Ile-His-Ala-Phe | SEQ ID NO: 28 |
| Analogue 11 | Asp-Arg-Val-Tyr-Ile-His-Pro-Tyr | SEQ ID NO: 29 |
| Analogue 12 | Pro-Arg-Val-Tyr-Ile-His-Pro-Phe | SEQ ID NO: 30 |
| Analogue 13 | Asp-Arg-Pro-Tyr-Ile-His-Pro-Phe | SEQ ID NO: 31 |
| Analogue 14 | Asp-Arg-Val-Tyr(Po$_3$)$_2$-Ile-His-Pro-Phe | SEQ ID NO: 32 |
| Analogue 15 | Asp-Arg-norLeu-Tyr-Ile-His-Pro-Phe | SEQ ID NO: 33 |
| Analogue 16 | Asp-Arg-Val-Tyr-norLeu-His-Pro-Phe | SEQ ID NO: 34 |
| Analogue 17 | Asp-Arg-Val-homoSer-Tyr-Ile-His-Pro-Phe | SEQ ID NO: 35 |

The polypeptides of the instant invention may be synthesized by a wide variety of methods such as those set forth in J. M. Stewart and J. D. Young, Solid Phase Peptide Synthesis, 2nd ed., Pierce Chemical Co., Rockford, Ill. (1984) and J. Meienhofer, Hormonal Proteins and Peptides, Vol. 2, Acaagents") as a therapeutic adjunct to erythropoietin treatment. The methods and kits of the present invention are clinically useful as a therapeutic adjunct for increasing red blood cell production in treating congenital or acquired aplastic or hypoplastic anemia.

The use of erythropoietin to promote erythropoiesis is well known in the art, as exemplified by Royet et al., U.S. Pat. No. 5,482,924; Goldberg et al., U.S. Pat. No. 5,188,828; Vance et al., U.S. Pat. No. 5,541,158; and Baertschi et al., U.S. Pat. No. 4,987,121, all references hereby incorporated in their entirety. The erythropoietin dosage regimen may vary widely, but can be determined routinely by a physician using standard methods. Dosage levels of the order of between about 1 EPO unit/kg and about 5,000 EPO units/kg body weight are useful for all methods of use disclosed herein.

In one embodiment, the effects of the active agents on the growth of erythroid progenitors in vitro are tested using the colony formation assay. The assay consists of growing erythroid progenitor cells in a semi-solid medium (methylcellulose) for two weeks (Yu et al., U.S. Pat. No. 5,032,507). Conditioned medium consisting of phytohemagglutinin-treated lymphocytes (PHA-LCM) is supplemented with erythropoietin and preferably, between about 0.1 ng/ml and about 10 mg/ml of the active agents.

The growth of erythroid precursors termed BFU-E (burst forming units erythroid) is monitored by identification and counting of the colonies under an inverted microscope as well as by staining of colonies (Yu et al., U.S. Pat. No. 5,032,507). The number of mixed colonies represents the number of earlier progenitor cells (containing erythroid as well as one or more other lineage cells).

In another embodiment, erythropoiesis is augmented ex vivo by obtaining a sample of bone marrow cells, as is known in the art, potentiating erythropoietin-induced differentiation with the active agents of the invention and infusing the treated cells back into the patient.

In a preferred embodiment, bone marrow cells are isolated from peripheral blood samples via standard techniques (U.S. Pat. Nos. 4,987,121, 5,104,653; hereby incorporated by reference in their entirety). $2 \times 10^6$ bone marrow cells are seeded in culture dishes in appropriate medium, such as modified Dulbecco's medium (IMDM) supplemented with (final concentration): horse serum (15%), fetal calf serum (5%), Fe saturated transferrin (0.4 mg/ml) hydrocortisone, penicillin 100 u/ml, and streptomycin (0.1 mg/ml) (Royet et al., U.S. Pat. No. 5,482,924). An adherent cell monolayer is formed. After 15 days, the non adherent cells are removed and fresh bone marrow is re-seeded in the presence of 0.1 U/ml of erythropoietin (EPO) and, preferably, between about 0.1 ng/ml and about 10 mg/ml of the active agents of the invention. The cells are expanded for a period of between 2 and 21 days with subsequent medium changes as required. Prior to reinfusion into the subject the cells are examined microscopically to verify the absence of contamination. The cells are rinsed to remove all traces of culture fluid, resuspended in an appropriate medium and then pelleted and rinsed several times. After the final rinse, the cells are resuspended at between $0.7 \times 10^6$ and $50 \times 10^6$ cells per ml in an appropriate medium and reinfused into a subject. Erythropoiesis is monitored by red cell count or hemoglobin concentration with time (Yu et al., U.S. Pat. No. 5,032,507, herein incorporated by reference in its entirety).

For use in increasing erythropoiesis in vivo, the active agents may be administered by any suitable route, including orally, parentally, by inhalation spray, rectally, transdermally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally.

Transdermal means including, but not limited to, transdermal patches may be utilized to deliver the active agents to the treatment site. Transdermal formulations may be prepared by incorporating the active agent in a thixotropic or gelatinous carrier including, but not limited to a cellulose medium, e.g., methyl cellulose or hydroxyethyl cellulose, with the resulting formulation then being packed in a transdermal device adapted to be secured in dermal contact with the skin of a wearer.

The active agents may be made up in a solid form (including granules, powders or suppositories) or in a liquid form (e.g., solutions, suspensions, or emulsions). The active agents may be subjected to conventional pharmaceutical operations such as sterilization and/or may contain conventional adjuvants, such as preservatives, stabilizers, wetting agents, emulsifiers, buffers etc.

While the active agents can be administered as the sole active pharmaceutical agent, they can also be used in combination with one or more other compounds. When administered as a combination, the active agent(s) and compound(s) can be formulated as separate compositions that are given at the same time or different times, or the active agent(s) and compound(s) can be given as a single composition.

For administration, the active agents are ordinarily combined with one or more adjuvants appropriate for the indicated route of administration. The active agents may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

Formulations suitable for topical administration include liquid or semi-liquid preparations suitable for penetration through the skin (e.g., liniments, lotions, ointments, creams, or pastes) and drops suitable for administration to the eye, ear, or nose.

The dosage regimen for augmenting erythropoiesis with the active agents is based on a variety of factors, including the type of injury, the age, weight, sex, medical condition of the individual, the severity of the condition, the route of administration, and the particular compound employed. Thus, the dosage regimen may vary widely, but can be determined routinely by a physician using standard methods. Dosage levels of the order of between 0.1 ng/kg and 10 mg/kg of the active agents per body weight are useful for all methods of use disclosed herein.

The treatment regime will vary depending on the disease being treated, based on a variety of factors, including the type of injury, the age, weight, sex, medical condition of the individual, the severity of the condition, the route of administration, and the particular compound employed.

In a preferred embodiment of the present invention, the active agents are administered intravenously. A suitable dose of the active agents is preferably between about 0.1 ng/kg and about 10 mg/kg administered twice daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

In another aspect, the present invention provides a novel peptide with erythropoiesis-promoting activity, consisting of the peptide with the sequence Asp-Arg-Lys-Tyr-Ile-His-Pro-Phe (SEQ ID NO:39).

A further object of the present invention is to provide pharmaceutical compositions comprising the active agents as an ingredient for use in the method of the invention. The compositions comprise the active agents together with erythropoietin and a pharmaceutically acceptable carrier, this term including any carrier which does not interfere with the effectiveness of the biological activity of the active agents and erythropoietin, and which is not toxic to the host to which it is administered. Dosage and administration of the pharmaceutical compositions will vary depending on the disease being treated, based on a variety of factors, including the type of injury, the age, weight, sex, medical condition of the individual, the severity of the condition, the route of administration, and the particular compound employed, as above. Thus, the dosage regimen may vary widely, but can be determined routinely by a physician using standard methods.

In a further aspect, the present invention provides kits promoting erythropoiesis, wherein the kits comprise an effective amount of the active agent, and instructions for using the amount effective of active agent as a therapeutic adjunct. In a preferred embodiment, the kit further comprises a pharmaceutically acceptable carrier, such as those adjuvants described above. In another preferred embodiment, the kit further comprises a means for delivery of the active agent to a mammal. Such devices include, but are not limited to matrical or micellar solutions, polyethylene glycol polymers, carboxymethyl cellulose preparations, crystalloid preparations (e.g., saline, Ringer's lactate solution, phosphate-buffered saline, etc.), viscoelastics, polyethylene glycols, and polypropylene glycols.

In a further preferred embodiment, the kits also comprise an amount of erythropoietin effective to accelerate erythropoiesis.

In another aspect of the present invention, an improved cell culture medium is provided for the promotion of erythropoiesis, wherein the improvement comprises addition to the cell culture medium of an effective amount of the active agents of the invention. Any cell culture media that can support erythropoiesis can be used with the present invention. Such cell culture media include, but are not limited to Basal Media Eagle, Dulbecco's Modified Eagle Medium, Iscove's Modified Dulbecco's Medium, McCoy's Medium, Minimum Essential Medium, F-10 Nutrient Mixtures, Opti-MEM® Reduced-Serum Medium, and RPMI Medium, or combinations thereof.

The improved cell culture medium can be supplied in either a concentrated (ie: 10×) or non-concentrated form, and may be supplied as a liquid, a powder, or a lyophilizate. The cell culture may be either chemically defined, or may contain a serum supplement. Culture media and serum supplements are commercially available from many sources, such as GIBCO BRL (Gaithersburg, Md.) and Sigma (St. Louis, Mo.).

The present invention, by providing methods and pharmaceutical compositions for augmenting erythropoiesis, will greatly increase the clinical benefits of treatment for congenital or acquired aplastic or hypoplastic anemia; amelioration of anemia associated with cancer, AIDS, chemotherapy, radiotherapy, bone marrow transplantation and chronic diseases.

The present invention may be better understood with reference to the accompanying examples that are intended for purposes of illustration only and should not be construed to limit the scope of the invention, as defined by the claims appended hereto.

Example 1

AII and AII Analogue and Fragment Effect on Erythroid Progenitor Formation

CD34+ cells were isolated from human cord blood by immunomagnetic chromatography using an antibody cocktail (Stem Cell Technologies, Vancouver BC) consisting of the following cell surface proteins: glycophorin A, CD56, CD66b, CD3, CD24, CD14, CD2, CD19, and CD16. Enriched cells were cultured at 37° at 5% $CO_2$ and air for 6 days in medium containing serum-free StemSpan (Stem Cell Technologies), 3 IU/ml human erythropoietin (EPO), 20 ng/ml stem cell factor, 20 ng/ml interleukin 3, and 20 ng/ml GM-CSF. The cells were harvested, counted and cultured in 96 well plates at a density of 50,000 cells per well in the same medium containing from 0 to 10 μg/ml of AII, AII analogues, or AII fragments. The peptides tested, and the figure showing the data received in those tests, are listed in Table 3. After 3 additional days in suspension culture (day 9), the cells were washed to remove the peptides and cultured to assess colony formation. The culture medium contained 0.9% methylcellulose in Iscove's MDM with 30% fetal calf serum, 1% bovine serum albumin, 10 μM 2-mercaptoethanol, 2 mM L-glutamine, 10% Agar Leukocyte Conditioned Medium with 3 IU/ml EPO. On days 2, 4, 9, and 14 the number and size of colonies was assessed as well as the number of BFU-E formed (burst forming units-erythroid) as a measure of erythropoiesis.

TABLE 3

Designation for Peptides Tested

| Name | Abbreviation | Sequence | FIG. | SEQ ID |
|---|---|---|---|---|
| 1GD | Ala$^4$-AII(1-7) | DRVAIHP | 1 | SEQ ID NO. 18 |
| GSD 24B | Pro$^3$-AII | DRPYIHPF | 2 | SEQ ID NO. 31 |
| 2GD | Pro$^3$-AII(1-7) | DRPYIHP | 3 | SEQ ID NO. 38 |
| 5GD | Lys$^3$-AII(1-7) | DRKYIHP | 4 | SEQ ID NO 39 |
| AII(1-7) |  | DRVYIHP | 5 | SEQ ID NO. 4 |
| AII |  | DRVYIHPF | 6 | SEQ ID NO. 1 |

The data from these experiments are presented in FIGS. 1-6 and show that each of the peptides tested increased the number of BFU-E formed relative to control where no peptide was added. Each of the peptides also increased the size of the colonies assessed (data not shown). Therefore, these data demonstrate that each of the peptides tested can be used to accelerate erythroid progenitor formation, and thus to promote erythropoiesis.

The methods and kits of the present invention are clinically useful as a therapeutic adjunct for increasing red blood cell production in treating congenital or acquired aplastic or hypoplastic anemia.

The present invention is not limited by the aforementioned particular preferred embodiments. It will occur to those ordinarily skilled in the art that various modifications may be made to the disclosed preferred embodiments without diverting from the concept of the invention. All such modifications are intended to be within the scope of the present invention.

We claim:

1. A method for treating anemia comprising administering to an anemic subject an amount effective of a peptide consisting of SEQ ID NO:4 to augment erythropoiesis.

2. The method of claim 1, wherein the anemia comprises aplastic anemia.

3. The method of claim 1, wherein the anemia comprises hypoplastic anemia.

4. The method of claim 1, further comprising contacting the erythroid progenitor cells with an amount effective to augment erythropoiesis of erythropoietin.

5. The method of claim 1, wherein the anemia is associated with chronic renal failure.

6. The method of claim 1, wherein the anemia is associated with end-stage renal disease.

7. The method of claim 1, wherein the anemia is associated with renal transplantation.

8. The method of claim 1, wherein the anemia is associated with cancer.

9. The method of claim 1, wherein the anemia is associated with acquired immune deficiency syndrome.

10. The method of claim 1, wherein the anemia is associated with chemotherapy.

11. The method of claim 1, wherein the anemia is associated with radiotherapy.

12. The method of claim 1, wherein the anemia is associated with bone marrow transplantation.

\* \* \* \* \*

SEQUENCE LISTING

<160> NUMBER OF SEQ ID NOS: 39

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Asp Arg Val Tyr Ile His Pro Phe
 1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Arg Val Tyr Ile His Pro Phe
 1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Val Tyr Ile His Pro Phe
 1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Asp Arg Val Tyr Ile His Pro
 1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Arg Val Tyr Ile His Pro
 1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

```
Val Tyr Ile His Pro
 1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Ile His Pro Phe
 1

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Asp Arg Val Tyr Ile His
 1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Asp Arg Val Tyr Ile
 1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic

<400> SEQUENCE: 10

Asp Arg Val Tyr
 1

<210> SEQ ID NO 11
<211> LENGTH: 3
<212> TYPE: PRT
<213> ORGANISM: Artificial Sequence
<220> FEATURE:
<223> OTHER INFORMATION: Synthetic

<400> SEQUENCE: 11

Asp Arg Val
 1

<210> SEQ ID NO 12
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)
<223> OTHER INFORMATION: Xaa is Nle
```

```
<400> SEQUENCE: 12

Arg Xaa Tyr Ile His Pro Phe
 1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)
<223> OTHER INFORMATION: Xaa is Nle

<400> SEQUENCE: 13

Arg Val Tyr Xaa His Pro Phe
 1               5

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

His Pro Phe
 1

<210> SEQ ID NO 15
<211> LENGTH: 5
<212> TYPE: PRT
<213> ORGANISM: Artificial Sequence
<220> FEATURE:
<223> OTHER INFORMATION: Synthetic

<400> SEQUENCE: 15

Tyr Ile His Pro Phe
 1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic
      class
<220> FEATURE:
<221> NAME/KEY: misc_feature
<222> LOCATION: (1)
<223> OTHER INFORMATION: Xaa at position 1 can be Arg, Lys, Ala, Orn,
      Ser, MeGly, D-Arg, or D-Lys
<220> FEATURE:
<221> NAME/KEY: misc_feature
<222> LOCATION: (2)
<223> OTHER INFORMATION: Xaa at position 2 can be Val, Ala, Leu, Nle,
      Ile, Gly, Pro, Aib, Acp, or Tyr
<220> FEATURE:
<221> NAME/KEY: misc_feature
<222> LOCATION: (4)
<223> OTHER INFORMATION: Xaa at position 4 can be Ile, Ala, Leu, Nle,
      Val, or Gly

<400> SEQUENCE: 16

Xaa Xaa Tyr Xaa His Pro Phe
 1               5
```

```
<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Arg Val Tyr Gly His Pro Phe
 1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

Arg Val Tyr Ala His Pro Phe
 1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic

<400> SEQUENCE: 19

Asp Arg Val Tyr Val His Pro Phe
 1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Asn Arg Val Tyr Val His Pro Phe
 1               5

<210> SEQ ID NO 21
<211> LENGTH: 11
<212> TYPE: PRT
<213> ORGANISM: Artificial Sequence
<220> FEATURE:
<223> OTHER INFORMATION: Synthetic

<400> SEQUENCE: 21

Ala Pro Gly Asp Arg Ile Tyr Val His Pro Phe
 1               5                   10

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Glu Arg Val Tyr Ile His Pro Phe
 1               5

<210> SEQ ID NO 23
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 23

Asp Lys Val Tyr Ile His Pro Phe
  1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Asp Arg Ala Tyr Ile His Pro Phe
  1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic

<400> SEQUENCE: 25

Asp Arg Val Thr Ile His Pro Phe
  1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Asp Arg Val Tyr Leu His Pro Phe
  1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

Asp Arg Val Tyr Ile Arg Pro Phe
  1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic

<400> SEQUENCE: 28

Asp Arg Val Tyr Ile His Ala Phe
  1               5

<210> SEQ ID NO 29
<211> LENGTH: 8
```

```
<212> TYPE: PRT
<213> ORGANISM: Artificial Sequence
<220> FEATURE:
<223> OTHER INFORMATION: Synthetic

<400> SEQUENCE: 29

Asp Arg Val Tyr Ile His Pro Tyr
 1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

Pro Arg Val Tyr Ile His Pro Phe
 1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic

<400> SEQUENCE: 31

Asp Arg Pro Tyr Ile His Pro Phe
 1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)
<223> OTHER INFORMATION: PHOSPHORYLATION

<400> SEQUENCE: 32

Asp Arg Val Tyr Ile His Pro Phe
 1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)
<223> OTHER INFORMATION: Xaa is Nle

<400> SEQUENCE: 33

Asp Arg Xaa Tyr Ile His Pro Phe
 1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (5)
<223> OTHER INFORMATION: Xaa is Nle

<400> SEQUENCE: 34

Asp Arg Val Tyr Xaa His Pro Phe
 1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)
<223> OTHER INFORMATION: homo Ser

<400> SEQUENCE: 35

Asp Arg Val Ser Tyr Ile His Pro Phe
 1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)
<223> OTHER INFORMATION: p-aminophenylalanine

<400> SEQUENCE: 36

Asp Arg Val Tyr Ile Xaa Pro Phe
 1               5

<210> SEQ ID NO 37
<211> LENGTH: 10
<212> TYPE: PRT
<213> ORGANISM: Artificial Sequence
<220> FEATURE:
<223> OTHER INFORMATION: Synthetic

<400> SEQUENCE: 37

Asp Arg Val Tyr Ile His Pro Phe His Leu
 1               5                  10

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Asp Arg Pro Tyr Ile His Pro
 1               5

<210> SEQ ID NO 39
<211> LENGTH: 7
<212> TYPE: PRT
<213> ORGANISM: Artificial Sequence
```

```
<220> FEATURE:
<223> OTHER INFORMATION: Synthetic

<400> SEQUENCE: 39

Asp Arg Lys Tyr Ile His Pro
 1               5
```